United States Patent [19]

Ichikawa et al.

[11] 4,151,204
[45] Apr. 24, 1979

[54] PROCESS FOR PREPARING AMINO ALCOHOLS

[75] Inventors: Yataro Ichikawa, Fuchu; Eishin Yoshisato; Koji Nakagawa, both of Iwakuni, all of Japan

[73] Assignee: Teijin Limited, Osaka, Japan

[21] Appl. No.: 771,674

[22] Filed: Feb. 24, 1977

Related U.S. Application Data

[63] Continuation-in-part of Ser. No. 590,945, Jun. 27, 1975, abandoned.

[51] Int. Cl.² ............... C07C 89/00; C07C 85/06; B01J 23/40
[52] U.S. Cl. .................... 260/584 R; 252/462; 252/463; 252/466 R; 252/470; 252/471; 252/472; 260/585 B
[58] Field of Search ............ 260/585 B, 584 R; 252/472

[56] References Cited

U.S. PATENT DOCUMENTS 3,270,059  8/1966  Winderl et al. ............ 260/585 B X
3,390,184  6/1968  Moss et al. ................. 260/585 B
3,766,184  10/1973  Johansson et al. ......... 260/584 R X Primary Examiner—Winston A. Douglas
Assistant Examiner—John Doll
Attorney, Agent, or Firm—Wenderoth, Lind & Ponack

[57] ABSTRACT

A process for preparing amino alcohols, which comprises reacting a polyhydric alcohol containing at least one primary alcoholic hydroxyl group and at least one secondary alcoholic hydroxyl group and expressed by the following general formula

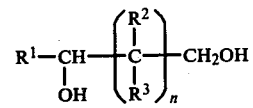

wherein $R^1$ is an alkyl group, $R^2$ and $R^3$ are identical or different and represent a hydrogen atom or a lower alkyl group an n is an integer of 0 to 3, with ammonia in the presence of specified hydrogenation catalyst thereby to aminate the secondary alcoholic hydroxyl group of the polyhydric alcohol selectively.

5 Claims, No Drawings

PROCESS FOR PREPARING AMINO ALCOHOLS

This application is a continuation-in-part application of U.S. Pat. Ser. No. 590,945 filed June 27, 1975 (now abandoned).

This invention relates to a process for preparing amino alcohols. More specifically, the invention relates to a process for preparing amino alcohols, which comprises reacting an aliphatic polyhydric alcohol containing at least one primary hydroxyl group and at least one secondary hydroxyl group in the same molecule, with ammonia to convert the secondary hydroxyl group of the polyhydric alcohol selectively to an amino group.

Various methods have previously been proposed for producing compounds having an alcoholic hydroxyl group and an amino group in the same molecule. With the prior art methods, however, it is relatively difficult to prepare amino alcohols containing a primary alcoholic hydroxyl group and an amino group bonded to the secondary carbon in the same molecule. For example, a reaction of an epoxide of a 1-olefin with ammonia easily affords an amino alcohol. But this reaction selectively yields an amino alcohol having an amino group bonded to the primary carbon, and an amino alcohol having a hydroxyl group bonded to the primary carbon, i.e. 2-amino1-ol, scarcely occurs. Thus, according to the conventional methods using 1-olefins or epoxides thereof as a starting material, it is extremely difficult to prepare 2-amino-1-ol selectively.

In order to obtain 2-amino-1-ol selectively on the basis of the conventional information, a complicated process is required which, for example, comprises adding formaldehyde to an aliphatic nitro compound having a nitro group at the terminal carbon to form a 2-nitro-1-ol, and then reducing it. Such a method is not commercially desirable.

On the other hand, various methods have previously been proposed for preparing aliphatic amines which comprise reacting aliphatic alcohols with ammonia in the presence of hydrogenation catalysts, preferably together with hydrogen, thereby to reduce the hydroxyl group of the alcohols to an amino group. It is known that Raney nickel, Raney cobalt, and reduced cobalt are effective catalysts that can be used in these methods. It is also known that such a reaction can be applied not only to aliphatic primary alcohols and aliphatic secondary alcohols, but also to other polyhydric alcohols such as ethylene glycol. However, studies have little been made as to the reductive amination of polyhydric alcohols containing a primary alcoholic hydroxyl group and a secondary alcoholic hydroxyl group in the same molecule, and it has not yet been clearly known what difference there is between the reactivities of these hydroxyl groups.

Accordingly, it is an object of this invention to provide a commercial process for preparing amino alcohols containing at least one hydroxyl group in the primary carbon and at least one amino group in the secondary carbon.

Another object of this invention is to provide a new process for preparing amino alcohols which comprises reacting a polyhydric alcohol containing at least one primary alcoholic hydroxyl group and at least one secondary alcoholic hydroxyl group in the same molecule, to convert the secondary alcoholic hydroxyl group in the polyhydric alcohol to an amino group.

The above objects can be achieved in accordance with this invention by a process for preparing amino alcohols which comprises reacting a polyhydric alcohol containing at least one primary alcoholic hydroxyl group and at least one secondary alcoholic hydroxyl group and expressed by the general formula

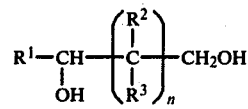

wherein $R_1$ is an alkyl group, $R^2$ and $R^3$ are identical or different and represent a hydrogen atom or a lower alkyl group and n is an integer of 0 to 3, with ammonia in the presence of a hydrogenation catalyst selected from the group consisting of a catalyst composed of cobalt and an oxide of a metal selected from the group consisting of iron, manganese, zinc, thorium, zirconium, lanthanum and uranium, and a catalyst composed of nickel and an oxide of a metal selected from the group consisting of iron, thorium and lanthanum thereby to aminate the secondary alcoholic hydroxyl group of the polyhydric alcohol selectively.

The aliphatic polyhydric alcohol used as a starting material in the process of the present invention contains at least one primary alcoholic hydroxyl group and at least one secondary alcoholic hydroxyl group in the same molecule. Specific examples of the polyhydric alcohols include aliphatic 1,2-glycols such as 1,2-propylene glycol, 1,2-butanediol, 3-methyl-1,2-butanediol, 1,2-pentanediol, 1,2-hexanediol, 1,2-decanediol, and 1,2-octadecanediol; or other glycols such as 1,3-butanediol, 2-methyl-1,3-butanediol, 2-methyl-1,3-pentanediol, 1,4-pentanediol, 1,3-hexanediol, 1,4-hexanediol, 1,4-heptanediol, and 2-isopropyl-1,3-butanediol; and trihydric alcohols such as glycerol, 1,2,4-butanetriol, and 1,2,6-hexanetriol. These polyhydric alcohols may contain at least one other substituent which does not retard the reaction, such as an amino, nitrile, amide, alkoxy, carboxyl, carboxylate ester, or tertiary alcohol group.

Polyhydric alcohols which give the best results in the process of this invention are those in which the primary alcoholic hydroxyl group and the secondary alcoholic hydroxyl group are attached to adjacent carbon atoms, such as 1,2-glycols. With these 1,2-glycols, the secondary alcoholic hydroxyl group can be converted to an amino group with very good selectivity. With other polyhydric alcohols, such as the 1,3-glycols or 1,4-glycols, in which the two types of hydroxyl group are spaced from each other by at least three carbon atoms, the selectivity tends to become somewhat lower.

It is interesting to note that when the process of this invention is applied to a primary aliphatic monoalcohol and a secondary aliphatic monoalcohol, there is no great difference in reactivity between them, and that when for example a mixture of these alcohols (e.g., a mixture of n-butanol and sec-butanol) is used in the reaction, there is hardly any different in reactivity between the primary monoalcohol and the secondary monoalcohol.

Surprisingly, it has been found that when the polyhydric alcohol, above all, 1,2- or 1,3-glycol, is reacted with ammonia in the presence of a hydrogenation catalyst in accordance with the process of this invention, the secondary alcoholic hydroxyl group of the polyhydric alcohol is converted to an amino group with a good selectivity, and aliphatic amino alcohols can be obtained in good yields.

Especially preferred polyhydric alcohols are those of the formula

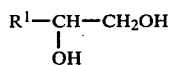

wherein $R^1$ is as defined above.

A tertiary alcoholic hydroxyl group, even if contained in the starting polyhydric alcohol, is noted aminated under the reaction conditions of this invention. Accordingly, polyhydric alcohols containing primary, secondary and tertiary alcoholic hydroxyl groups at the same time can be converted to amino alcohols as a result of the amination of only the secondary alcoholic hydroxyl group with a high selectivity.

The reaction in accordance with this invention is carried out in the presence of a hydrogenation catalyst. Any catalysts having activity in hydrogenation reactions can be used in the present invention. Preferred catalysts have the ability to induce hydrogenation and dehydrogenation. Examples of suitable catalysts are reducible metals such as nickel, cobalt or copper, and noble metals such as platinum, palladium, ruthenium, and rhenium. Of these, the nickel-type or cobalt-type hydrogenation catalysts are especially superior. Specific examples of the cobalt-type catalysts are Raney cobalt, reduced cobalt or Urushibara cobalt, and specific examples of the nickel-type catalysts are Raney nickel, reduced nickel and Urushibara nickel. Of these, the reduced cobalt catalyst and the reduced nickel catalyst are especially superior.

We have found that by using a catalyst consisting of the above cobalt-type hydrogenation catalyst or the nickel-type hydrogenation catalyst and a small amount of another metal or metal oxide, amino alcohols can be obtained in high yields and selectivities at a temperature of not more than 200° C. Examples of suitable metals or metal components are iron, manganese, magnesium, aluminum, zinc, barium, cesium, thorium, cerium, zirconium, lanthanum, and uranium. The use of the additive metal or metal oxide has an effect of markedly increasing the catalytic acitivity of the cobalt catalyst or nickel catalyst, and prolonging the active lifetime of the catalyst.

A catalyst composed of cobalt and an oxide of a metal selected from the group consisting or iron, manganese, zinc, thorium, zirconium, lanthanum and urenium, or a catalyst composed of nickel and an oxide of a metal selected from the group consisting of iron, thorium and lanthanum is especially superior.

The amount of the additive metal or metal oxide varies according to the type of the metal, the form of the catalyst, or the method of preparation of catalyst (for example, the temperature at which the catalyst is calcined), but in terms of an atomic ratio to cobalt or nickel, it is 0.01–1, preferably 0.01–0.6 for iron, 0.001–0.3, preferably 0.005–0.2 for cesium, lanthanum and zirconium, 0.001–0.20, preferably 0.02–0.10 for uranium and thorium, and not more than 0.3, preferably not more than 0.2, for manganese, magnesium, zinc, aluminum, barium, cesium, thallium, and other metals.

If the amount is less than this range, the effect is small, and if it exceeds the above range, side-reactions such as a decomposition reaction may take place vigorously.

The reduced cobalt catalyst and reduced nickel catalyst containing the above additive can be prepared by various catalyst preparation methods of which a precipitating method and a calcining method are preferred.

The precipitating method comprises neutralizing a mixed solution of a cobalt or nickel salt and a salt of the additive metal, with an aqueous solution of an alkali such as sodium hydroxide, sodium carbonate or ammonium carbonate to form a precipitate, washing the precipitate with water, drying or calcining it, and then reducing it in a stream of a hydrogen gas at a temperature of 250° to 450° C.

On the other hand, the calcining method involves pyrolyzing the above salt mixture to an oxide, and reducing the oxide in a stream of hydrogen at 250° to 450° C.

The catalyst of this invention may be supported on a known carrier such as silica, alumina, diatomaceous earth, kaolin, carborundum, or silicon carbide.

Since the activity of the catalyst of this invention can be maintained for a longer period of time in the presence of hydrogen, the reaction is performed preferably in the presence of hydrogen. Advantageously, the partial pressure of hydrogen is at least 1 atmosphere, preferably 10 to 30 atmospheres.

The reaction temperature is affected by various factors such as the type of the catalyst used, but is usually 100° to 300° C., preferably 120° to 250° C. The desired amino alcohol can be obtained more selectively when the reaction is carried out at a relatively low temperature within the above range using a catalyst having the highest possible activity. At relatively high temperatures, there is an increased formation of a by-product resulting from the amination of the primary alcoholic hydroxyl group of the starting material, and marked side-reactions tend to occur such as the conversion of the resulting amines to secondary amines or the hydrogenating decomposition of the resulting amines. From this standpoint, the most preferred temperature is 120° to 200° C.

Preferably, the amount of ammonia is stoichiometrically in excess of the polyhydric alcohol, because small amounts lead to the formation of larger amounts of by-products such as secondary or tertiary amines. For example, it is at least 3 moles, preferably at least 5 moles, per mole of the starting polyhydric alcohol.

The reaction in accordance with this invention can be performed either in the vapor phase or in the liquid phase, but is preferably carried out in the liquid phase.

The reaction can also be carried out in the presence of a solvent. Examples of the solvent are hydrocarbons such as n-hexane, cyclohexane, benzene, toluene or xylene, ethers such as diethyl ether, tetrahydrofuran or dioxane, esters such as ethyl acetate, amides such as dimethylformamide or dimethylacetamide, and nitriles such as acetonitrile, all of which are inert to the reaction. The amount of the solvent is not particularly restricted.

When the reaction is carried out in the liquid phase, the process can be performed either continuously or batchwise using a pressure reactor. The reaction pressure in this case is desirably 100 to 600 atmospheres although varying according to the reaction temperature, the type and proportion of the starting substances, or the presence or absence of the solvent. The preferred partial pressure of hydrogen is 10 to 300 atmospheres.

On the other hand, when the reaction is carried out in the vapor phase, the pressure may be either reduced, atmospheric, or elevated. Generally, it is desirable to perform the reaction at atmospheric pressure or a pressure near it. The vapor-phase reaction can be performed by vaporizing the starting material, mixing it with ammonia gas, preferably further with hydrogen gas, and heating the resulting gaseous mixture to a temperature in the above range, followed by contacting it with the catalyst.

The amino alcohols obtained by the present invention are useful as medicines and their intermediates.

The following Examples illustrate the process of this invention in greater detail without any intention of limiting the invention thereto.

EXAMPLES 1 TO 4

A 300 ml. vertically stirred autoclave was charged with 1.8 g (0.2 mole) of 1,2-butanediol, 85 g (5 moles) of ammonia and each of the Raney catalysts shown in Table I, and hydrogen was introduced to a pressure of 30 atmospheres at room temperature.

The temperature was raised, and the reaction was carried out at a prescribed temperature for a prescribed period as indicated in Table I. After the reaction, ammonia was driven off, and the product was quantitatively analyzed by gas-chromatography. The results are shown in Table I.

Table I

| Example No. | Catalyst | Temperature (°C.) | Time (hr) | Conversion of 1,2-butanediol (hrs) | Selectivity of 2-aminobutanol (%) | Mole ratio of 2-aminobutanol to 1-aminobutanol |
|---|---|---|---|---|---|---|
| 1 | Raney Co. | 220 | 3 | 69 | 21 | 5.0 |
| 2 | Raney Ni (A) | 220 | 3 | 50 | 27 | 2.8 |
| 3 | Raney Ni (B) | 220 | 3 | 75 | 19 | 1.1 |
| 4 | Raney Cu | 200 | 2 | 8 | 54 | 2.2 |

The Raney nickel (A) was prepared by developing a powder of an alloy containing Ni and Al in a ratio of 30 to 70. The Raney nickel (B) was prepared by developing a powder of an alloy containing Ni and Al in a ratio of 50 to 50.

In this and following Examples, the conversion of 1,2-butanediol and the selectivity of 2-aminobutanol were calculated in accordance with the following equations.

$$\text{Conversion of 1,2-butanediol} = \frac{\text{(Moles of 1,2-butanediol used in the reaction)} - \text{(Moles of 1,2-butanediol recovered)}}{\text{Moles of 1,2-butanediol used in the reaction}} \times 100$$

$$\text{Selectivity of 2-aminobutanol} = \frac{\text{(Moles of 2-aminobutanol formed)}}{\text{(Moles of 1,2-butanediol used in the reaction)} - \text{(Moles of 1,2-butanediol recovered)}} \times 100$$

EXAMPLES 5 TO 7

A reduced cobalt catalyst was prepared as follows:

106 g of sodium carbonate ($Na_2CO_3$) was dissolved in 2 liters of water, and with stirring, a solution of 292 g of cobalt nitrate [$Co(NO_3)_2 \cdot 6H_2O$] in 2 liters of water was added dropwise to the resulting solution over the course of about 2 hours. After the addition, the mixture was allowed to stand overnight, washed several times by decantation, filtered, and then dried overnight at 110° C. The dried powder was pyrolyzed at 300° C., molded into tablets with a size of about 5 mm in diameter and about 2 mm in thickness, and then reduced in a stream of hydrogen kept at about 350° C.

Using 10 g of the resulting catalyst, each of the starting polyhydric alcohols shown in Table II was reductively aminated in the same autoclave as used in Example 1. The amount of the starting polyhydric alcohol was 0.3 mole, and the amount of ammonia was 6.0 moles. The reaction was carried out at 180° C. for 3 hours. The initial partial pressure of hydrogen at room temperature was 50 atmospheres. The results obtained are shown in Table II.

Table II

| Example No. | Starting alcohol | Conversion of the starting material (%) | Selectivity of 2-amino-1-ol (%) | Hole ratio of 2-amino-1-ol to 1-amino-2-ol |
|---|---|---|---|---|
| 5 | 1,2-propylene glycol | 34 | 57 | 11.3 |
| 6 | 1,2-butanediol | 51 | 55 | 5.4 |
| 7 | 1,3-butanediol | 57 | 39*1) | 2.0*2) |

*1)Selectivity of 3-amino-1-ol
*2)Mole ratio of 3-amino-1-ol to 1-amino-3-ol

EXAMPLES 8 TO 10

Commercially available cobalt oxide was molded into tablets each having a thickness of 2 mm and a diameter of 6 mm, calcined at 1350° C. for 1 hour, and reduced in a stream of hydrogen to 300° to 350° C. to prepare a calcined reduced cobalt. Using 10 g of this catalyst, propylene glycol or 1,2-butanediol was reacted in a 300 ml. autoclave. The amount of the starting alcohol was 0.3 mole, and the amount of ammonia was 5.0 moles. The initial partial pressure of hydrogen was 50 atmospheres. The reaction was carried out for 3 hours at each of the temperatures indicated in Table III. The results are shown in Table III.

Table III

| Example No. | Starting alcohol | Reaction temperature (°C.) | Conversion of the starting material (%) | Selectivity of 2-amino-1-ol (%) | Mole ratio of 2-amino-1-ol to 1-amino-2-ol |
|---|---|---|---|---|---|
| 8 | 1,2-propanediol | 200 | 52 | 60 | 4.9 |
| 9 | 1,2-butanediol | 180 | 21 | 71 | 5.3 |
| 10 | 1,2-butanediol | 200 | 44 | 54 | 4.0 |

EXAMPLES 11 TO 39

With stirring, a solution of 109 g (1.03 moles) of sodium carbonate ($Na_2CO_3$) in 2 liters of water was added dropwise to a solution of 277 g (0.95 mole) of cobalt nitrate [$Co(NO_3)_2 \cdot 6H_2O$] and 20 g (0.05 mole) of ferric nitrate [$Fe(NO_3)_3 \cdot 9H_2O$] in 2 liters of water. The resulting precipitate was treated in the same way as in the preparation of reduced cobalt in Examples 5 to 7 to form a Co—$Fe_2O_3$ catalyst (Co/Fe atomic ratio 95/5). By the same precipitating method, catalysts containing various metal oxides were prepared. Using 10 g of each of the catalysts so prepared, 3.0 moles of 1,2-butanediol was reacted with 6.0 moles of ammonia in a 300 ml. vertically stirred autoclave. The initial partial pressure of hydrogen was 50 atmosphere. The results are shown in Table IV.

Table IV

| Example No. | Catalysts (atomic ratio) | Reaction temperature (°C.) | Conversion of 1,2-butanediol (%) | Selectivity of 2-amino-butanol (%) | Mole ratio of 2-amino-butanol to 1-amino-butanol |
|---|---|---|---|---|---|
| 11 | Co-MgO (95-5) | 180 | 22 | 60 | 5.3 |
| 12 | " | 200 | 54 | 50 | 3.6 |
| 13 | Co-ZnO (90-10) | 160 | 9 | 43 | 15.3 |
| 14 | " | 180 | 58 | 43 | 7.2 |
| 15 | Co-MnO (95-5) | 180 | 18 | 77 | 11.0 |
| 16 | " | 200 | 51 | 37 | 4.8 |
| 17 | Co-$ZrO_2$ (95-5) | 160 | 67 | 56 | 8.6 |
| 18 | " | 180 | 84 | 12 | 6.6 |
| 19 | Co-$La_2O_3$ (95-5) | 140 | 34 | 78 | 25.6 |
| 20 | " | 160 | 68 | 79 | 10.3 |
| 21 | Co-$Fe_2O$ (99-1) | 180 | 33 | 65 | 3.8 |
| 22 | " | 200 | 72 | 33 | 3.7 |
| 23 | Co-$Fe_2O_3$ (95-5) | 160 | 17 | 93 | 13.8 |
| 24 | " | 180 | 55 | 81 | 9.6 |
| 25 | Co-$Fe_2O_3$ (90-10) | 160 | 26 | 93 | 13.6 |
| 26 | " | 180 | 61 | 85 | 9.9 |
| 27 | Co-$FeO_3$ (50-50) | 200 | 18 | 32 | 7.7 |
| 28 | " | 220 | 40 | 50 | 4.0 |
| 29 | Co-$Cs_2O$ (95-5) | 180 | 21 | 73 | 4.6 |
| 30 | Co-BaO (95-5) | 160 | 21 | 70 | 4.7 |
| 31 | Co-$UO_2$ (98.2) | 140 | 31 | 70 | 11.4 |
| 32 | " | 160 | 65 | 84 | 9.9 |
| 33 | Co-$ThO_2$ (98-2) | 140 | 61 | 76 | 21.2 |
| 34 | Co-$ThO_2$ (99-1) | 160 | 65 | 92 | 20.0 |
| 35 | Co-ThO (99.5-0.5) | 160 | 65 | 91 | 21.9 |
| 36 | Co-T10 (98-2) | 170 | 15 | 81 | 4.7 |
| 37 | Co-ZnO (98-2) | 180 | 17 | 84 | 9.4 |
| 38 | Co-$ThO_2$-$Fe_2O_3$ (97-1-2) | 140 | 32 | 72 | 18.8 |
| 39 | " | 160 | 64 | 86 | 14.5 |

EXAMPLES 40 TO 45

Using a catalyst consisting of cobalt prepared in the same way as in Examples 11 to 38 and a small amount of each of various metal oxide, 1,2-propylene glycol was reductively aminated. The results are shown in Table V.

Table V

| Ex. No. | Catalyst | Reaction temperature (°C.) | Conversion of 1,2-propylene glycol (%) | Selectivity of 2-amino propanol (%) | Mole ratio of 2-amino propanol to 1-amino propanol |
|---|---|---|---|---|---|
| 40 | Co-$ZrO_2$ (99-1) | 180 | 63 | 51 | 4.6 |
| 41 | Co-T10 (98-2) | 180 | 39 | 54 | 6.4 |
| 42 | Co-ZnO (98-2) | 180 | 33 | 48 | 15.9 |
| 43 | Co-$ThO_2$ (99-1) | 180 | 96 | 52 | 6.5 |
| 44 | Co-$La_2O_3$ (95-5) | 160 | 62 | 76 | 13.2 |
| 45 | Co-$Fe_2O_3$ (95-5) | 170 | 62 | 50 | 18.5 |

REFERENTIAL EXAMPLE 1

Using the same Co-$La_2O_3$ (95-5) as used in Examples 19 and 44, a mixture of 0.2 mole of n-butanol ($CH_3CH_2CH_2OH$) and 0.2 mole of sec-butanol [$CH_3CH_2CH(OH)CH_3$] was reacted at 140° C. for 3 hours with 6.0 moles of ammonia in a 300 ml. vertically stirred autoclave using hydrogen at an initial pressure of 50 atmosphere.

After the reaction, the product was analyzed by gas-chromatography. It was found that the conversion of n-butanol was 32%, and the selectivity of n-butylamine was 84%, and that the conversion of sec.-butanol was 35%, and the selectivity of sec.-butylamine was 80%. Accordingly, the ratio of the conversion of sec.-butanol to that of n-butanol was about 1.1, and the ratio of the yield of sec.-butylamine to that of n-butylamine was 1.04.

EXAMPLES 46 TO 55

Catalysts were prepared by adding a small amount of each of the metal oxides shown in Table VI to nickel in the same way as in the preparation of cobalt metal oxide catalysts. Using each of the resulting catalysts, 1,2-butanediol was reductively aminated. The results are shown in Table VI.

Table VI

| Ex. No. | Catalyst | Reaction temperature (°C.) | Conversion of 1,2-butanediol (%) | Selectivity of 2-amino-butanol (%) | Mole ratio of 2-amino-butanol to 1-amino-butanol |
|---|---|---|---|---|---|
| 46 | Ni-$Fe_2O_3$ (90-10) | 180 | 17 | 43 | 4.9 |
| 47 | " | 200 | 37 | 46 | 3.2 |
| 48 | Ni-$Fe_2O_3$ (80-20) | 160 | 20 | 43 | 14.4 |
| 49 | " | 180 | 40 | 71 | 9.7 |
| 50 | " | 200 | 72 | 61 | 6.2 |
| 51 | Ni-$ThO_2$ (99-1) | 160 | 19 | 53 | 24.3 |
| 52 | " | 180 | 36 | 62 | 15.1 |
| 53 | Ni-$La_2O_3$ (95-5) | 140 | 18 | 47 | 36.9 |
| 54 | " | 160 | 41 | 91 | 18.5 |

Table VI-continued

| Ex. No. | Catalyst | Reaction temperature (°C.) | Conversion of 1,2-butanediol (%) | Selectivity of 2-amino-butanol (%) | Mole ratio of 2-amino-butanol to 1-amino-butanol |
|---|---|---|---|---|---|
| 55 | " | 180 | 60 | 76 | 10.7 |

EXAMPLES 56 TO 58

Using 5 g of each of commercially available 5% Pt on carbon, 5% Pd on carbon, and 0.5% Ru on carbon, 0.25 mole of 1,2-butanediol was reacted with 5.0 moles of ammonia at 200° C. for 3 hours using hydrogen at an initial pressure of 50 atmospheres in a 300 ml. autoclave. The results are shown in Table VII. In all cases, considerable amounts of secondary amines were formed as by-products.

Table VII

| Ex. No. | Catalyst | Conversion of 1,2-butanediol (%) | Selectivity of 2-amino-butanol (%) | Mole ratio of 2-aminobutanol to 1-amino-butanol |
|---|---|---|---|---|
| 56 | 5% Pt on C | 48 | 7.7 | 2.1 |
| 57 | 5% Pd on C | 34 | 2.4 | 1.8 |
| 58 | 0.5% Ru on C | 84 | 6.1 | 21.0 |

EXAMPLE 59

This Example illustrates the preparation of 2-amino-1-butanol from 1,2-butanediol by the vapor-phase process.

(a) Preparation of Catalyst

A solution of 263 g (0.9 mole) of cobalt nitrate [Co(NO$_3$)$_2$.6H$_2$O] and 24 g (0.1 mole) of copper nitrate [Cu(NO$_3$)$_2$.3H$_2$O] in 2 liters of water was added dropwise with stirring to a solution of 106 g (1.0 mole) of sodium carbonate (Na$_2$CO$_3$) in 2 liters of water. The resulting precipitate was allowed to stand overnight, washed with water, dried, calcined, and molded into tablets. The tablets were reduced in a steam of hydrogen at 200° to 250° C. to prepare a catalyst with a composition Co-Cu (90–10).

(b) Procedure of Reaction 40 g of the above catalyst was filled in the central portion of a reaction tube with a diameter of 20 mm and a length of 1 m, and the temperature of the catalyst layer was maintained at 180° C.

1,2-Butanediol was vaporized at a rate of 5 g/hour, and mixed with 0.10 liter/min. of ammonia gas and 0.25 liter/min. of hydrogen gas. The gaseous mixture was pre-heated to 180° C., and passed into the catalyst layer. The reacted gas which passed through the catalyst layer was collected on a dry ice-methanol cooling medium, and quantitatively analyzed by gas-chromatography.

It was found that the conversion of 1,2-butanediol was 50%, and the selectivity of 2-amino-1-butanol was 8%. 1-Amino-2-butanol was scarcely detected, but considerable amounts of by-product secondary amines were formed.

What we claim is:

1. A process for preparing amino alcohols, which comprises reacting a dihydroxy alcohol containing one primary alcoholic hydroxyl group and one secondary alcoholic hydroxyl group and expressed by the following formula

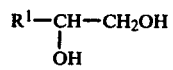

wherein R$^1$ is an alkyl group,
with ammonia in the presence of a hydrogenation catalyst selected from the group consisting of a catalyst composed of cobalt and an oxide of a metal selected from the group consisting of iron, manganese, zinc, thorium, zirconium, lanthanum and uranium, and a catalyst composed of nickel and an oxide of a metal selected from the group consisting of iron, thorium and lanthanum thereby to selectively produce a monoamino-monoalcohol expressed by the following formula

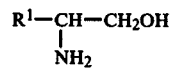

wherein R$^1$ is as defined above,
the amount of ammonia employed in the amination being at least 3 moles per mole of the starting dihydroxy alcohol.

2. A process according to claim 1 wherein the said hydrogenation catalyst is supported on a carrier.

3. A process according to claim 1 wherein the reaction is carried out in the presence of hydrogen.

4. A process according to claim 1 wherein the reaction is carried out at a temperature of from 100° to 300° C.

5. A process according to claim 1 wherein the polyhydric alcohol is 1,2-butanediol.

* * * * *